Figure 1:
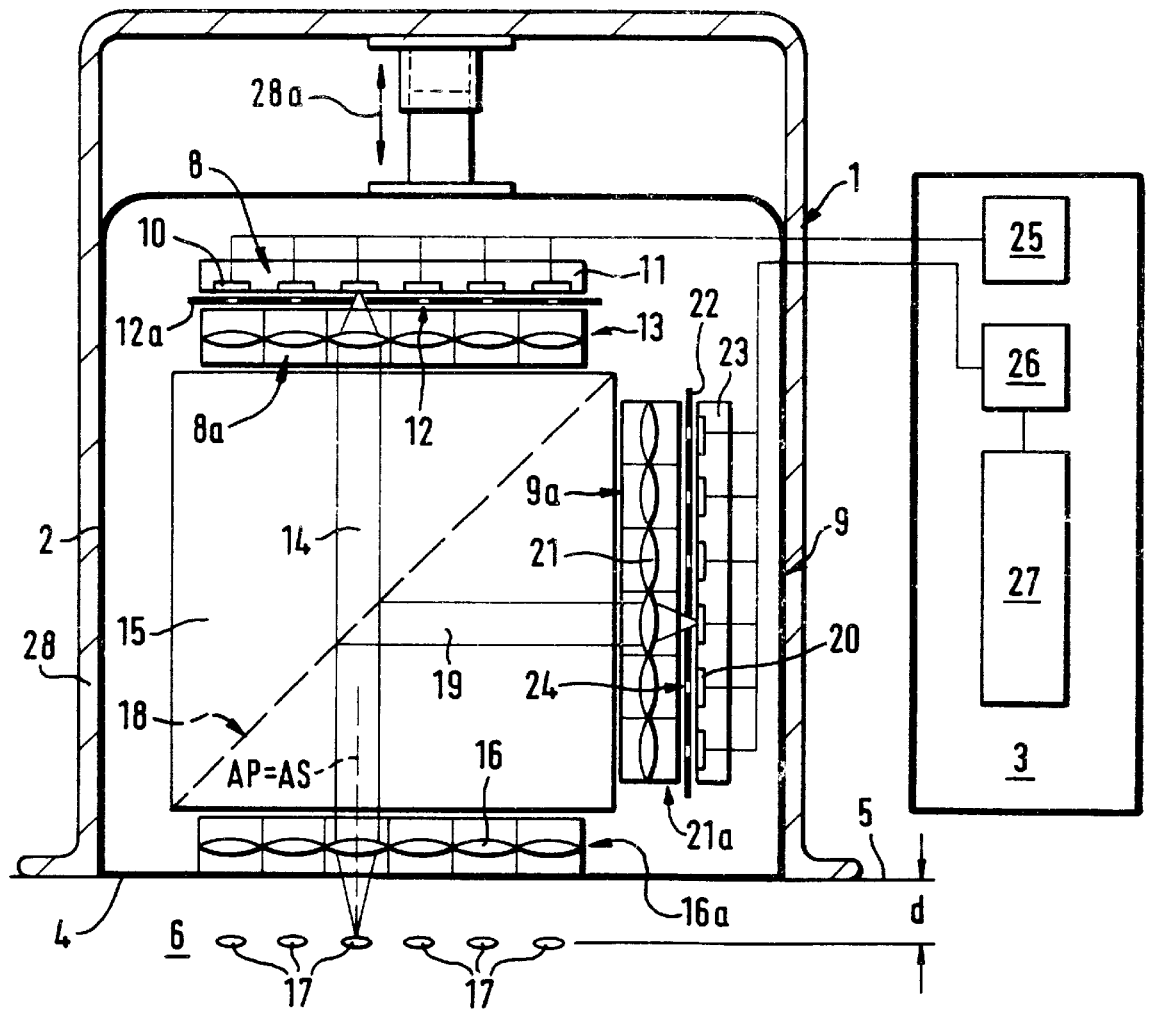

United States Patent [19]
Knuettel et al.

[11] Patent Number: 5,962,852
[45] Date of Patent: Oct. 5, 1999

[54] PROCESS AND DEVICE FOR DETERMINING AN ANALYTE CONTAINED IN A SCATTERING MATRIX

[75] Inventors: Alexander Knuettel, Weinheim; Dirk Boecker, Heidelberg; Matthias Essenpreis, Gauting, all of Germany

[73] Assignee: Roche Diagnostics GmbH, Mannheim, Germany

[21] Appl. No.: 08/875,349

[22] PCT Filed: Jan. 23, 1997

[86] PCT No.: PCT/DE97/00168

§ 371 Date: Jul. 28, 1997

§ 102(e) Date: Jul. 28, 1997

[87] PCT Pub. No.: WO97/27469

PCT Pub. Date: Jul. 31, 1997

[30] Foreign Application Priority Data

Jan. 26, 1996 [DE] Germany .......................... 196 02 656

[51] Int. Cl.⁶ .................................................. G01N 21/49
[52] U.S. Cl. ...................................... 250/339.11; 356/345
[58] Field of Search ........................ 356/345; 250/339.11

[56] References Cited

U.S. PATENT DOCUMENTS

| | | | |
|---|---|---|---|
| 5,203,328 | 4/1993 | Samuels et al. | 600/319 |
| 5,555,087 | 9/1996 | Miyagawa et al. | 356/345 |
| 5,565,986 | 10/1996 | Knüttel | 356/346 |
| 5,579,112 | 11/1996 | Sugiyama et al. | 356/360 |

OTHER PUBLICATIONS

Optics Letters, vol. 11, No. 3, Mar., 1986, "Femotosecond Optical Ranging in Biological Systems", Fujimoto et al pp. 150–152.

Applied Optics, vol. 32, No. 26, Sep. 10, 1993, "Time–Resolved Fourier Spectrum and Imaging in Highly Scattering Media", Wang et al pp. 5043–5048.

Biophys. J., Biophysical Society, vol. 44, Dec., 1983, pp. 315–324, "A Continuously Variable Frequency Cross–Correlation Phase Fluorometer With Picosecond Resolution", Gratton et al.

Applied Optics, vol. 32, No. 30, Oct. 20, 1993, "Measurement of Optical Properties of Biological Tissues by Low–Coherence Reflectometry", Schmitt et al pp. 6032–6042.

SPIE–The International Society for Optical Engineering, vol. 1889, 197–211, "Optical Characterization of Dense Tissues Using Low–Coherence Interferometry", Schmitt et al Jan. 1993.

*Primary Examiner*—Constantine Hannaher
*Attorney, Agent, or Firm*—Nikaido, Marmelstein, Murray & Oram LLP

[57] ABSTRACT

Method for determining an analyte in a scattering matrix. In a detection step detection measurements are made in which light is irradiated into the matrix as primary light and light leaving the scattering matrix is detected as secondary light, in order to determine as a measurement quantity a measurable physical property of the light which is variable due to the interaction of the light with the matrix. Information on the presence of the analyte in the matrix is determined in an evaluation step. The determination of optically weakly absorbing analytes against a strongly absorbing interference background is improved by the use of two selection methods for the depth selective detection of the secondary light in combination with one another. Primary light is focused by means of a primary light optically focussing element onto a region of focus lying in the matrix at a predetermined measuring depth and the region of focus is imaged by means of a secondary light optically focusing element onto a light entry aperture arranged in the light path of the secondary light to the detector. In addition to this first depth selection by a confocal arrangement, a second depth selection device is used to detect light reflected from a defined measuring depth as secondary light, with the measuring depth coinciding with the depth of focus.

29 Claims, 7 Drawing Sheets

PROCESS AND DEVICE FOR DETERMINING AN ANALYTE CONTAINED IN A SCATTERING MATRIX

The invention relates to a method and an apparatus for analysing a scattering matrix with respect to an analyte contained therein by means of light.

The most important application of the invention is the analytical investigation of biological samples, in particular of the tissue of a living organism. Biological samples are mostly optically heterogeneous, i.e. they contain a large number of scattering centres at which irradiated light is scattered. This applies to human or animal tissue, in particular skin tissue or subcutaneous fatty tissue, but also to fluid biological samples, such as blood for example, in which the blood corpuscles form scattering centres, or else to milk, in which the scattering centres are formed by emulsified fat droplets.

Furthermore the invention is directed towards scattering matrices in general in which an analyte is to be determined qualitatively or quantitatively. A scattering matrix in this sense is a three-dimensional structure with such a high density of optical scattering centres that irradiated light is generally scattered many times before it leaves the scattering matrix again. Non-biological scattering matrices which can be investigated on the basis of the present invention are for example emulsions and dispersions such as are required for various purposes, for example for paints and varnishes.

Reference will be made below, without restriction of the general concept, to the analysis of tissue as an example of biological and other scattering matrices.

The object of the analytical methods towards which the invention is directed is the determination of an analyte in the sense that information on the presence of a particular component contained in the tissue is obtained. The information can relate to the concentration of the analyte (quantitative analysis) or simply to the question whether the analyte is contained (in a concentration above the detection limit of the method) in the sample (qualitative analysis).

Analyses of tissues and other biological samples have to date mainly been carried out invasively, i.e. a sample (mostly a blood sample) is removed from the tissue, and the analyte concentration therein is determined by means of reagents.

There has been increasing discussion in recent times of non-invasive methods of analysis, in which the analytical result is determined painlessly and without reagents from the tissue without sampling. Most of the methods discussed for this purpose are based on the interaction of light with the scattering matrix. In all of these methods, measurement steps are carried out in which light is irradiated into the matrix as primary light through an interface bordering the matrix and light leaving the matrix is detected as secondary light. The purpose of this is to measure a measurable physical property of the light which varies due to the interaction of the light with the matrix and which correlates with the concentration of the analyte in the matrix. Such a procedural step will be described here as the "detection step" and the measurement as the "detection measurement". A detection step may include one or more detection measurements.

The wavelengths of light which are discussed for such methods lie in general between about 300 nanometers (nm) and several thousand nanometers, i.e. in the spectral range between near-UV and infrared light. The physical property of light which can be determined (detected) in the detection step, which can also be described as the "quantifiable parameter", will be described below as the "measurement quantity" for the sake of simplicity.

An absolute measurement of the analyte concentration is generally not possible with the methods discussed here. Therefore a calibration is required (as with most of the analytical methods based on chemical reactions). In at least one calibration step, which is performed with the same measuring techniques as a detection step, at least one detection measurement is carried out on a scattering matrix with a known analyte concentration. In the analysis of living tissue, this takes place with advantage by means of a comparison measurement using any known analytical method.

In an evaluation step of the analytical method the analyte concentration is determined from the change in the measurement quantity in at least one detection step in comparison with at least one calibration step. The evaluation step incorporates an evaluation algorithm, in which the analyte concentration is determined in a predetermined manner from the results of at least one detection step and at least one calibration step.

Most of the methods of this kind are based on the principles of spectroscopy, i.e. on the investigation of the spectral dependence of the optical absorption. To this end detection measurements are carried out at at least two different wavelengths of light. Whereas in a clear fluid this is a well-established trouble-free method, the spectroscopic analysis of tissue and other scattering matrices is very difficult.

Firstly, the useful signal (the change in the absorption spectrum as a function of a change in the analyte concentration) is very small for most analytes, and the said small useful signal is accompanied by a considerable noise background resulting in particular from the optical absorption of water and other strongly absorbing components (inter alia the red blood pigment haemoglobin).

Secondly, there exists in a scattering matrix, by virtue of the multiple scattering of the light, the problem that the optical path length travelled by the light in the sample is unknown. A knowledge of this path length is however a prerequisite for being able to determine the concentration of an analyte according to Lambert-Beer's law during a spectroscopic analysis.

Many attempts of various kinds have been made to solve these problems. In particular, comparison techniques are applied, in which an attempt is made to eliminate the influence of strongly absorbing interfering substances and also the influence of the multiple scattering and resulting absence of knowledge of the optical path length, by a plurality of detection measurements and the calculation of ratios or differences. The problem of the unknown optical path length is specifically addressed by time-resolved spectroscopy.

Despite these efforts, the spectroscopic analysis of tissue has acquired practical importance for only one analyte, namely the red blood pigment haemoglobin (Hb or its oxidized form $HbO_2$). These substances are so strongly absorbent and are present in such high concentrations that a spectroscopic determination with the known methods is possible. It is precisely this strong optical absorption, however, that is a fundamental reason why the spectroscopic analysis of other analytes has been unsuccessful to date.

Glucose is a particularly important analyte, because if diabetics are to be treated successfully over a long period, the glucose levels in the body have to be monitored continuously as far as possible. In order to prevent serious late traumas such as blindness or amputation of limbs, for example, the glucose concentration has to be determined at least five times a day. This is scarcely possible with invasive methods.

The optical absorption of the tissue depends to only a very small extent, however, on the glucose concentration. Spectroscopic principles have therefore not been successful. Various alternative methods for the non-invasive determination of the glucose concentration are being discussed.

For example, in European patent specification 0 074 428 it is assumed that the glucose molecules scatter a beam of light transmitted through a glucose solution in a characteristic manner and that the glucose concentration can be determined from the solid angle distribution of the transmitted light intensity leaving a test cuvette or a body part under investigation. In WO 94/10901 the spatial distribution of the secondary light intensity at the interface is determined as a measure of the glucose concentration, and it is explained that the said spatial distribution depends in a characteristic manner on the glucose concentration in a tissue sample. The reason for this is that because of the multiple scattering in the tissue the glucose concentration influences to a surprisingly high degree the spatial distribution of the secondary light leaving the interface. DE 4 243 142 A1 describes a method for determining the glucose concentration in the anterior chamber of the eye, in which the optical absorption and the rotation of polarized irradiated light are described as measurement quantities. In WO 95/30368 various possibilities are described for determining the glucose concentration on the basis of LCI (Low Coherence Interferometry) measurements, in which inter alia the scattering coefficient and the index of refraction, both of which depend on the glucose concentration, are discussed as measurement quantities.

The methods described in these publications are important starting points for solving the problems associated with non-invasive analysis in tissue samples. They are limited, however, to a particular analyte, namely glucose. Also for principle reasons the selectivity is relatively small.

The invention is directed to the object of providing a method and an apparatus for analysing tissue or other optically strongly scattering matrices. Said method should make it possible to analyse selectively an analyte contained therein even if the total optical absorption of the scattering matrix is influenced to only a very small extent by the concentration of the analyte.

The object is achieved, with a method incorporating at least one detection step and at least one evaluation step in the sense explained above, by the fact that two selection methods are used in combination with one another for the selective detection of secondary light coming from a defined measuring depth of the sample:

Firstly, the primary light is focussed by means of an optically focussing element onto a region of focus, and the region of focus is imaged by means of an optically focussing element onto a light entry aperture disposed in the light path of the secondary light to the detector, so that the detection of the secondary light is concentrated on the region of focus.

Secondly, an additional depth selection means is used to detect selectively, as secondary light, light reflected from a defined measuring depth which coincides with the depth of focus. In particular a low coherence reflectometric measuring method or a "time-gating" method is used as an additional depth selection means.

The invention also provides an apparatus for carrying out such a method with a measuring head with a sample contact surface for placing against an interface of the scattering matrix, light irradiation means with a light transmitter for irradiating primary light into the scattering matrix through the sample contact surface and the interface, detection means with a detector for detecting secondary light leaving the scattering matrix through the interface and the sample contact surface, and evaluation means for deriving information on the presence of the analyte in the matrix from the measuring signal of the detector, in which the irradiation means and the detection means each comprise an optically focussing element, the optically focussing element of the irradiation means focusses the primary light onto a region of focus in the matrix at a depth of focus below the interface and the optically focussing element of the detection means images the region of focus onto a light entry aperture disposed in the light path of the secondary light to the detector, whereby the detection of the secondary light is concentrated on the region of focus. An additional depth selection means is provided for detecting, as secondary light, light reflected selectively from a defined measuring depth, wherein the measuring depth coincides with the depth of focus.

An arrangement in which an object is illuminated with light focussed onto a focal point (focus) and the observation is concentrated on the same focus is designated as a "confocal arrangement". Such a confocal arrangement is known for various purposes, for example from the following references:

1) C. J. R. Sheppard et al.: "Imaging performance of confocal fluorescence microscopes with finite-sized source", Journal of Modern Optics, 41 (1994), pp. 1521–1530.
2) U.S. Pat. No. 5,192,980
3) U.S. Pat. No. 5,345,306
4) EP 0689045

Since in the confocal arrangement the light is concentrated on the region of focus at a particular depth of focus and the detection is also concentrated on the same region of focus, the confocal arrangement results in a certain depth selection. The detector detects selectively photons which are reflected at a distance from the interface which corresponds to the depth of focus of the confocal arrangement. In order to obtain the advantageous results of the present invention, it is necessary however to employ an additional depth selection means by means of which light reflected from a defined measuring depth coinciding with the depth of focus is detected selectively as secondary light. As mentioned, a time-gating method is suitable. Particularly preferred, however, is an additional depth selection using a low coherence reflectometric measuring method.

As a result of the confocal arrangement, photons which are scattered in the matrix on the path from the focus to the interface and are thus deflected do not reach the detector through the light entry aperture disposed in front of the detector in the light path. The signal of the detector is therefore predominantly indicative of photons which are reflected from a structure in the region of the focus in the scattering matrix and which leave the matrix unscattered.

In practice it is not possible to focus the primary light onto a geometric point in the matrix and to concentrate the imaging on the same geometric point. Rather is it inevitable, given optical imaging errors and the finite size both of the light source and the detector-side light entry aperture, that the confocal arrangement will cover a partial volume of the matrix with a finite size. This partial volume is named here the "region of focus".

When the method according to the invention and the corresponding apparatus are used, changes in the concentration of an analyte which causes only a very small share of the total optical absorption lead to a relatively strong change in the measuring signal. Therefore even with such difficult analytes a selective analysis is possible. This is true in particular in a wavelength range in which the analyte has an absorption band.

The invention will be described in greater detail below by means of embodiments shown in the figures.

Figure 2A:
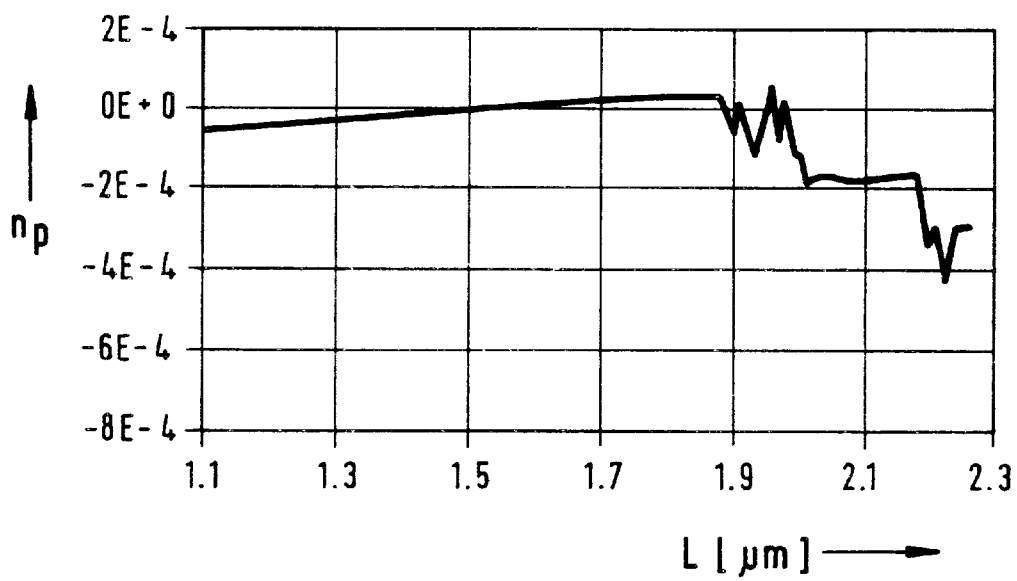
Figure 2B:
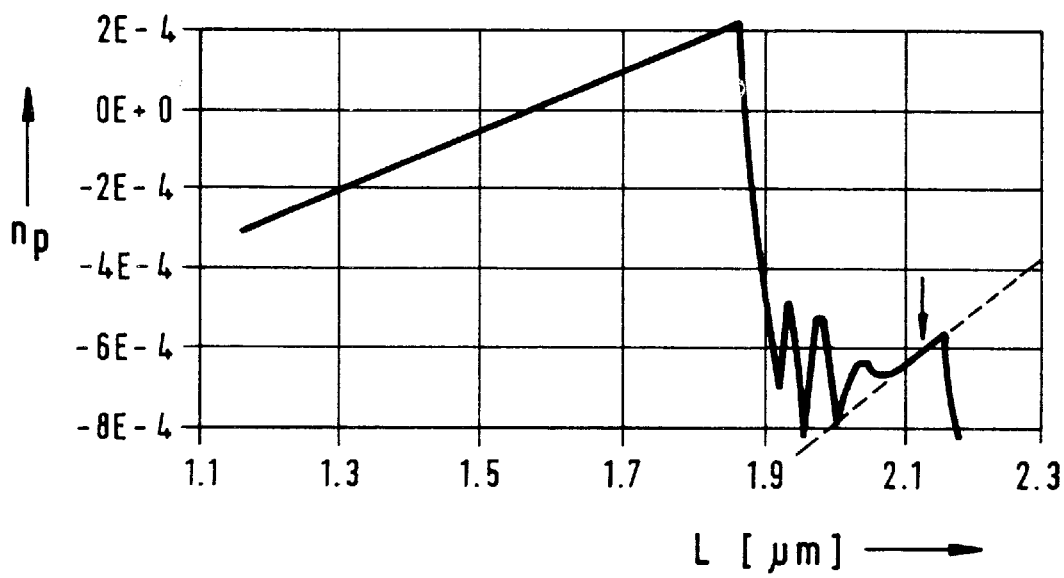
Figure 3:
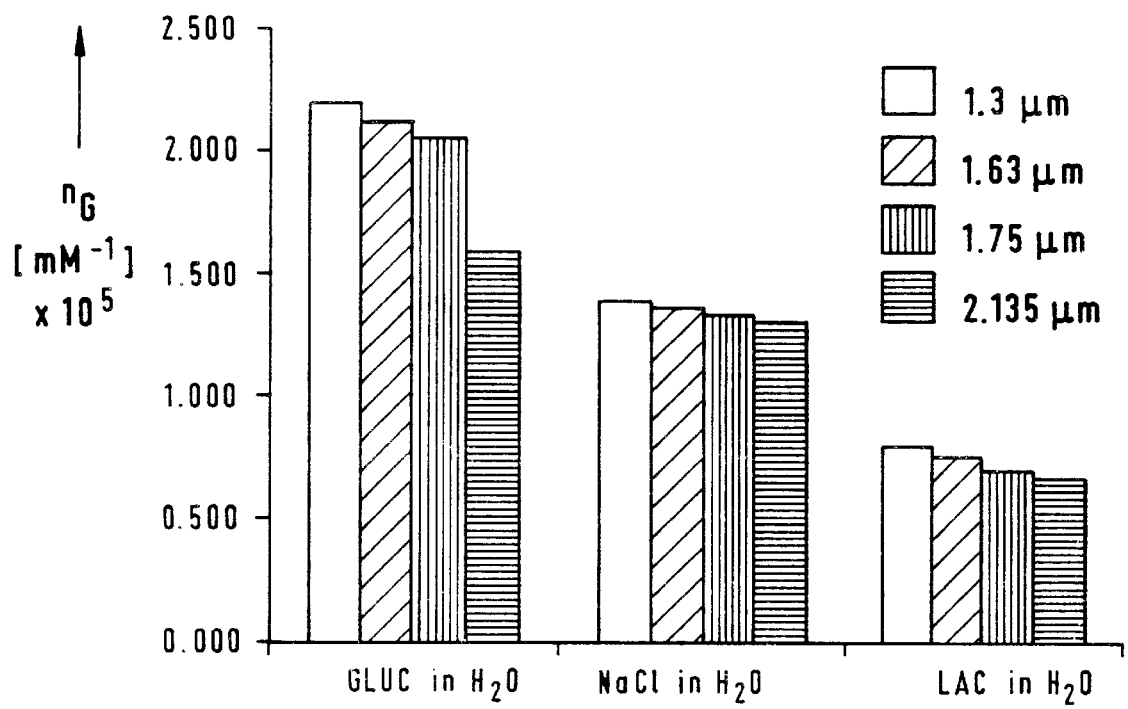
Figure 4:
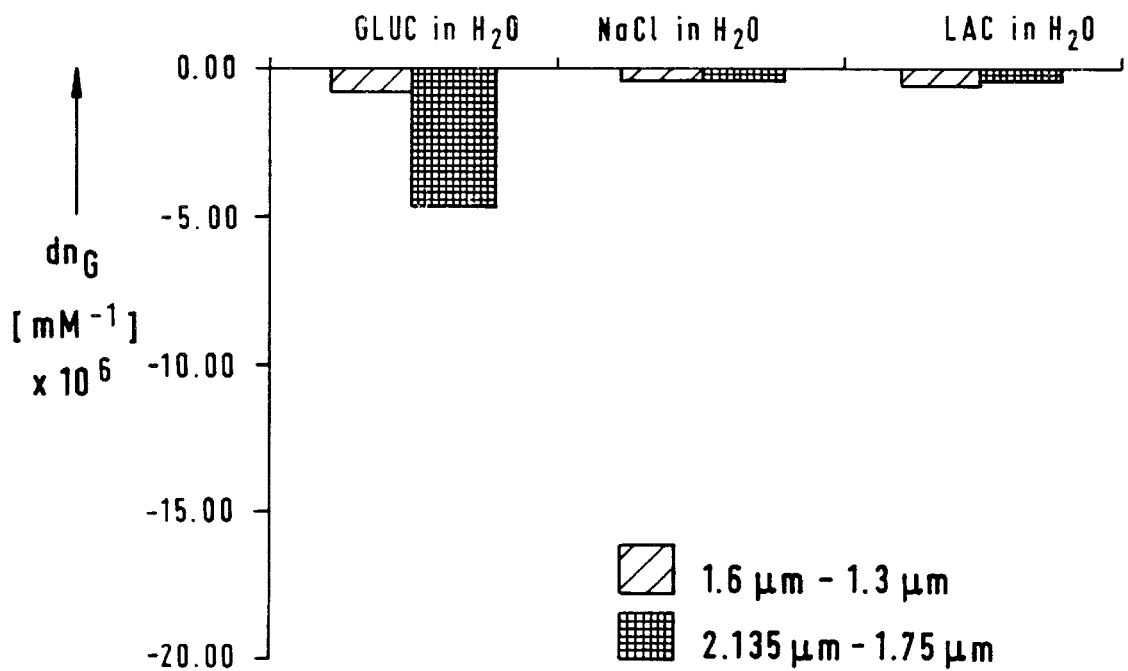
Figure 5:
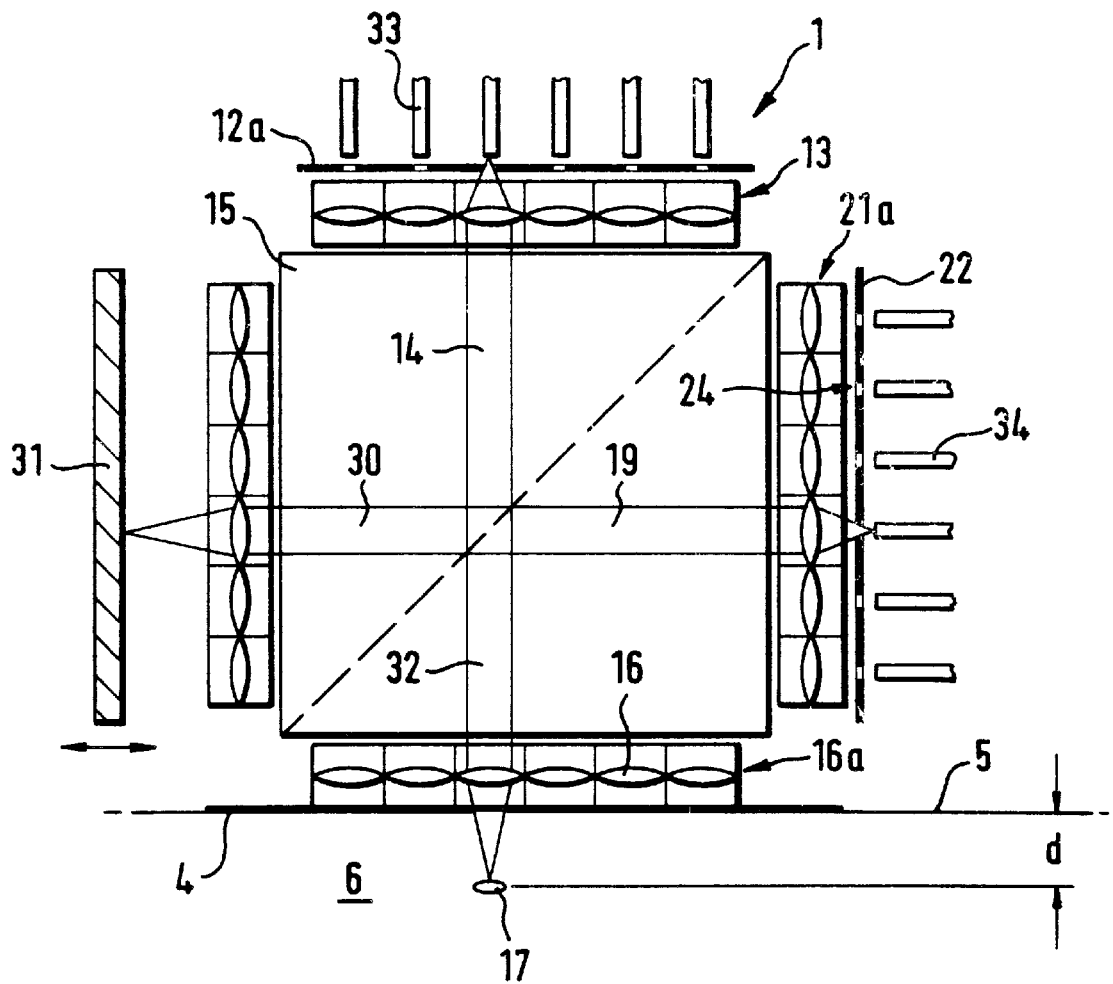
Figure 6:
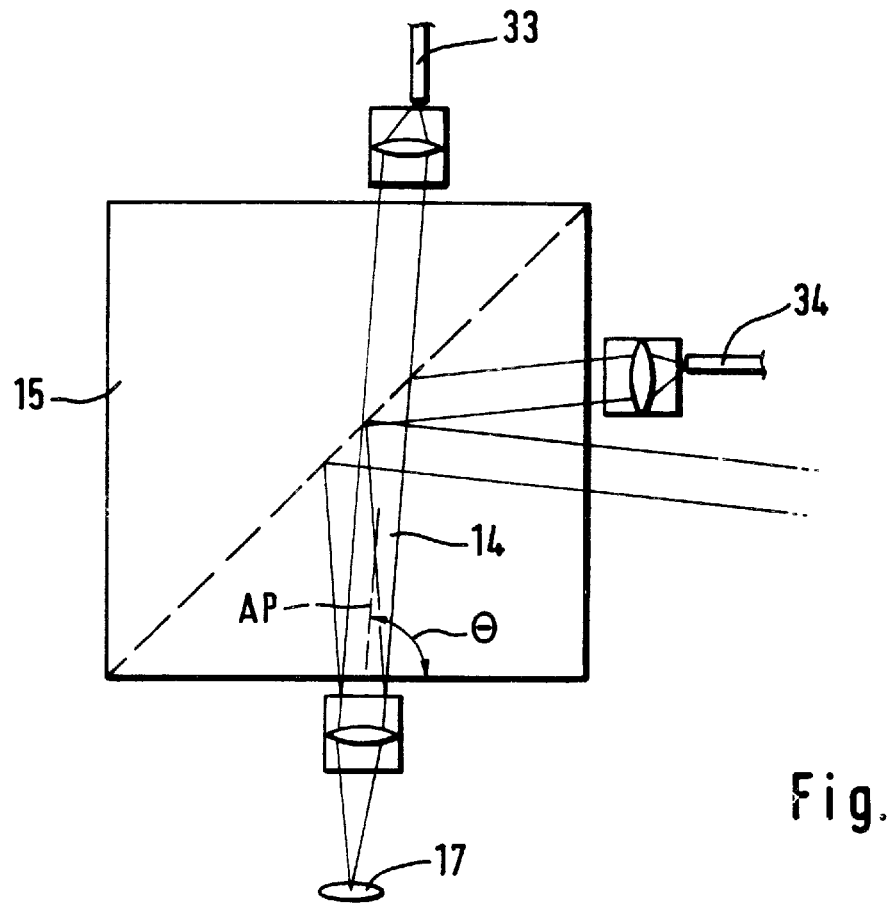
Figure 7:
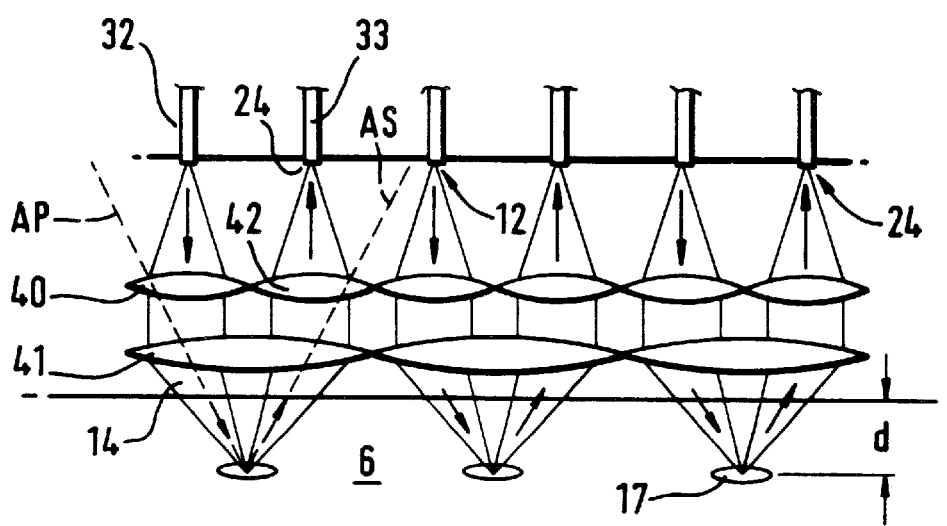
Figure 8:
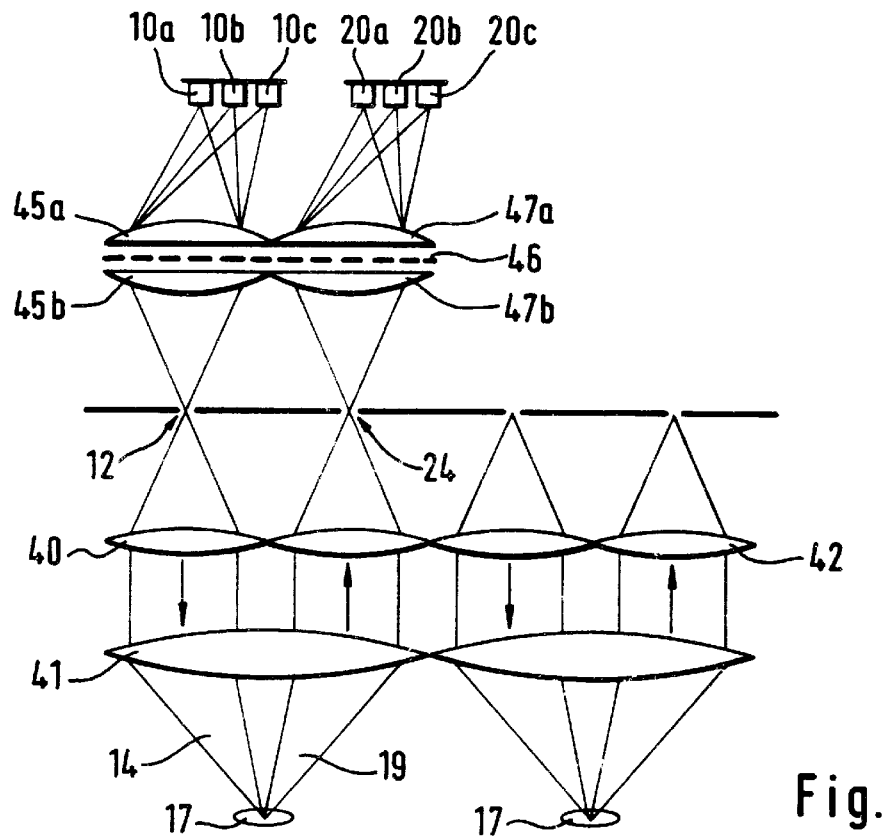
Figure 9:
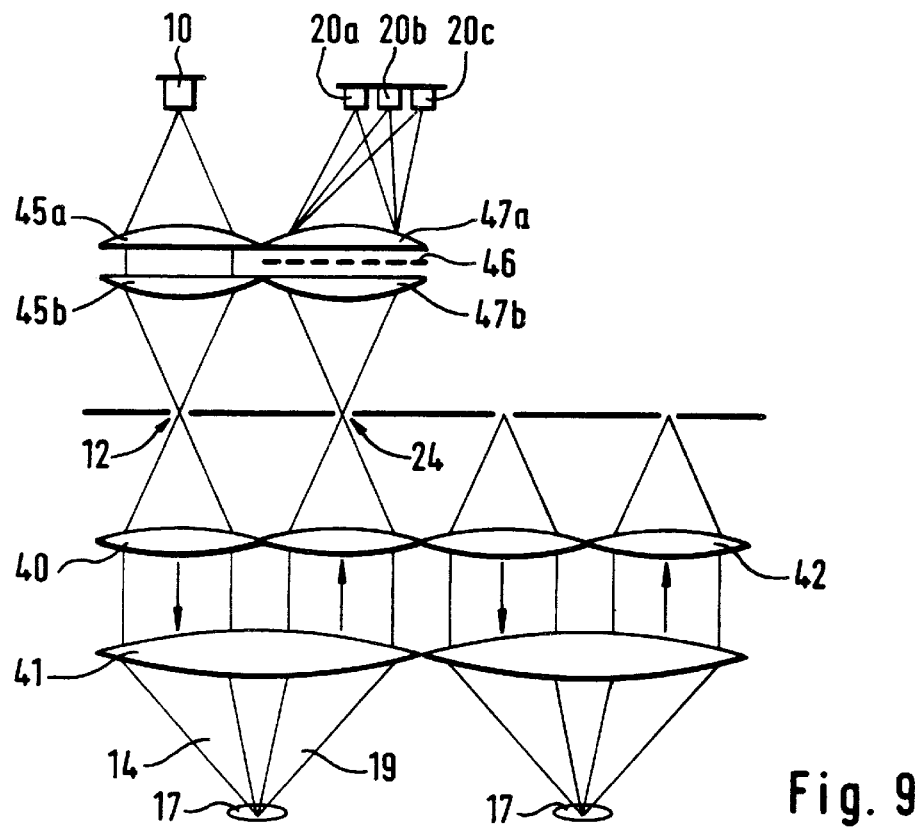
Figure 10:
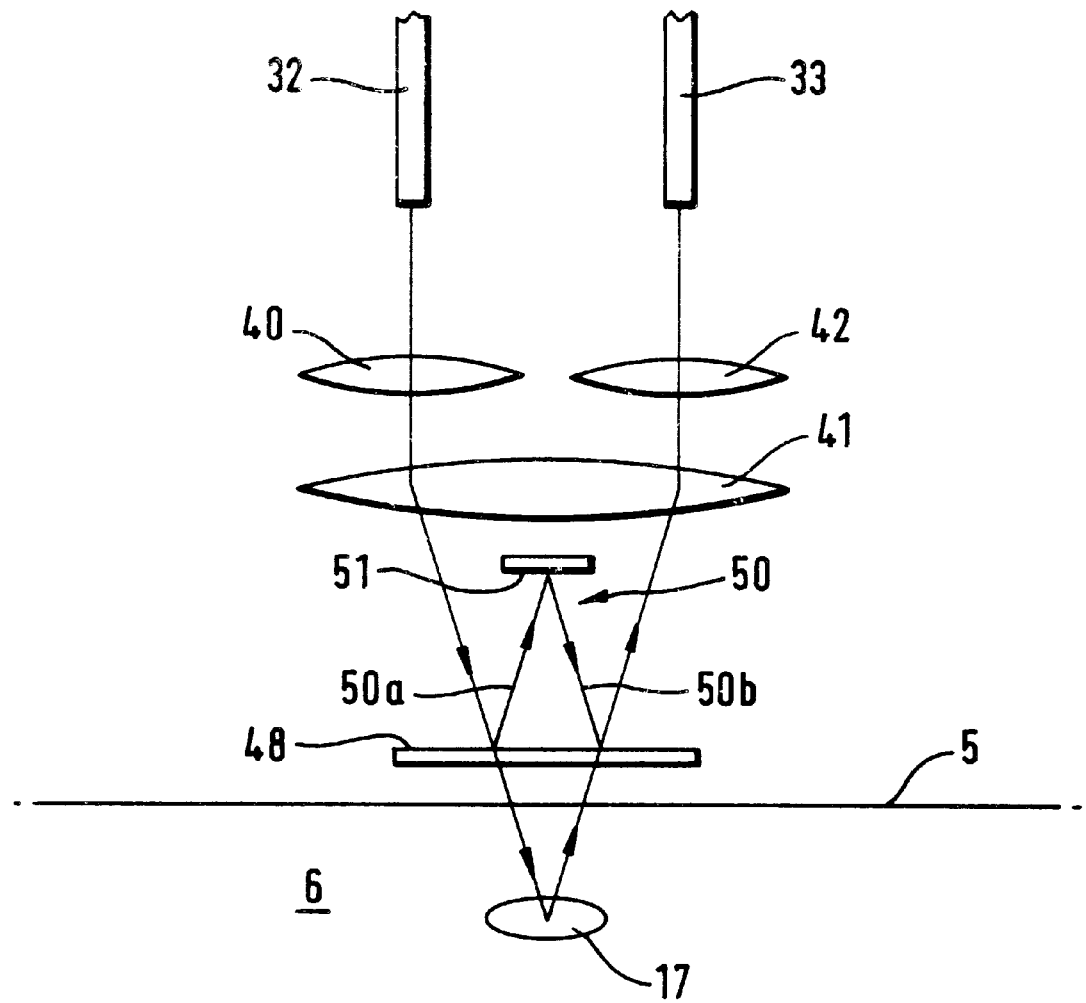

FIG. 1 shows a block diagram of an analysis apparatus according to the invention, FIGS. 2a and 2b shows graphs of the dependence of the phase refractive index on the light wavelength for two different concentrations of a glucose solution in water, FIG. 3 shows a bar chart of the group refractive index of glucose and of two interfering substances, each dissolved in water, for four different wavelengths of light, FIG. 4 shows the differential group refractive index for the substances of FIG. 3 and two wavelength pairs in each case, FIG. 5 shows part of an alternative embodiment of an analysis apparatus in a schematic cross-sectional diagram, FIG. 6 shows a schematic cross-sectional diagram of a further embodiment, FIG. 7 shows a schematic cross-sectional diagram of a further embodiment, FIGS. 8 and 9 show two schematic cross-sectional diagrams of different embodiments allowing a spectrally resolved measurement at several light wavelengths and FIG. 10 shows a schematic cross-sectional diagram of an embodiment further modified on the basis of FIG. 7.

The analysis apparatus 1 shown highly schematised in FIG. 1, partly in section and partly as a block diagram, consists essentially of a measuring head 2 and an electronic unit 3. The measuring head 2 lies with a sample contact surface 4 against the interface 5 of a scattering matrix 6 (e.g. against the surface of human skin). In the measuring head 2 are located light irradiation means 8 for irradiating primary light 14 into the matrix 6 and detection means 9 for detecting secondary light 19 leaving the matrix 6.

The light irradiation means 8 incorporate several light trans-mitters 10, to each of which is assigned an optical system 8a (formed in the case shown by the lenses 13 and 16) by means of which the primary light 14 is focussed onto a region of focus 17 lying in the tissue at a predetermined depth d of the matrix. In the embodiment shown, a plurality of semiconductor light transmitters (light-emitting diodes) are integrated monolithically in a semiconductor substrate (chip) 11. In order to allow good focussing, the light transmitters 10 should be as small as possible. Pinhole diaphragms 12a are located in front of the light transmitters 10 in order to restrict the light exit apertures 12.

The divergent light leaving the light exit apertures 12 is collimated by an arrangement of collimation lenses 13 and enters a beam splitter cube (BSC) 15 as a parallel beam of light. The light leaving the opposite surface of the BSC 15 is focussed onto the region of focus 17 by a focussing lens 16.

The light irradiation means, consisting of the light transmitters 10 and the components 12, 13 and 16, are present in multiple form (n-fold) and are disposed as a (preferably regular) array 18 parallel to the interface 5 of the matrix 6 in such a way that primary light beams 14 are focussed onto a plurality of regions of focus 17 which preferably lie at the same measuring depth d in the tissue 6. In FIG. 1 for the sake of clarity the light path is shown for only one of the regions of focus 17.

The secondary light leaving each of the regions of focus 17 is collimated by the lenses 16 and falls back coaxially into the primary beam. In the BSC 15 the beam is divided such that the secondary light is reflected in the direction of a detector 20 perpendicularly to the direction of the primary light beam 14. A further lens 21 and a pinhole diaphragm 22, which form the detector-side light entry aperture 24, are located in front of the detector 20. The lenses 16 and 21 together form an optical imaging system 9a by means of which the region of focus 17 is imaged onto the light entry aperture 24 (strictly speaking onto the plane of the detector-side light entry aperture 24).

The detectors 20 are present n-fold in the same number as the light transmitters 10 and are disposed as an array matching the light transmitters, with an optical system 16, 21 being assigned to each detector 20. Preferably semiconductor detectors (for example avalanche photodiodes) are used, which are integrated monolithically on a common semiconductor substrate 23. The collimator lenses 13, the focussing lenses 16 and the imaging lenses 21 disposed in front of the detectors 20 are preferably embodied as a "microlens array" (16a, 21a). Microlens arrays of this kind are commercially available.

The optical systems 8a and 9a, which form part of the light irradiation means 8 and of the detection means 9, can be embodied in a different manner in such a way that the irradiation and imaging conditions explained are attained. In particular, instead of the single lenses shown, multi-lens systems (objectives), and in principle also mirrors can be used.

The light irradiation means 8 allow to generate in the scattering matrix, with the use of an optically focussing element (here the focussing lens 16), an optical focus in the region of focus 17. A result of the confocal arrangement of the detection means 9 is (as explained above) that mainly photons reflected in the region of focus 17 are detected by the detectors 20 and only a small proportion of diffusely scattered light reaches the detector 20.

The electronic unit 3 contains a power supply circuit 25 for the light transmitters 10, an amplifier circuit 26 for amplifying the output signal of the detectors 20 and an evaluation unit 27 realised conventionally by means of a microprocessor, which provides the desired analytical information from the measuring signals of the detectors 20.

In order to provide by means of a "time-gating" method an additional means of depth selection (i.e. for the selective detection of photons which have been reflected at a measuring depth coinciding with the depth of focus d), the power supply circuit 25 generates extremely short signal pulses, which are converted into very short light pulses by the light transmitters 10. The amplifier circuit 26 and the evaluation unit 27 are adapted to selectively detect within a defined time window, which corresponds to the desired measuring depth d, the secondary light received by the detectors 20. Considering the extremely short light travel times and the required precision, the means required for this are complex, but are at any rate available. A required control line for transmitting a trigger signal is labelled 25a in FIG. 1. More detailed information on various technologies suitable for such measurements can be obtained from the relevant literature. In particular the following publications may be mentioned the contents of which are incorporated into the present application text by reference:

5) "Femtosecond optical ranging in biological systems", by J. G. Fujimoto et al., OPTICS LETTERS, 1986, 150–152.

6) "Time-resolved Fourier spectrum and imaging in highly scattering media", by L. Wang et al., APPLIED OPTICS, 1993, 5043 ff.

7) "A continuously variable frequency cross-correlation phase fluorometer with picosecond resolution", by E. Gratton et al., BIOPHYSICAL JOURNAL, 1983, 315–324.

Preferably in the invention a plurality of measurements are made with different depths of focus d. To this end the measuring head 2 is movable in a direction perpendicular to the interface 5. Advantageously this vertical positioning can be produced by means of a frame-type holding member 28 supported on the interface 5 of the scattering matrix 6 and by means of a positioning drive which is shown symbolically as a double arrow 28a in FIG. 1.

Due to the combination of measurement techniques according to the invention the measuring signal of the detectors 20 relates essentially only to photons which have been reflected at a defined measuring depth d and pass essentially unscattered from there to the respective detector 20. Unscattered photons are also named "ballistic" photons. The arrangement according to the invention also, however, detects photons which are scattered through a small mean scattering angle. The path (propagation path) of such photons runs in the vicinity of the geometric light path, and therefore deviates only minimally from the shortest (ballistic) path. Photons of this kind are named "quasi-ballistic". The arrangement according to the invention can thus be designated as a "depth-selective quasi-ballistic measuring regime".

According to the present knowledge of the inventors, the following grounds can be given for the advantages of this depth-selective quasi-ballistic measuring regime in the determination of an analyte in a scattering, in particular biological, matrix.

The ballistic or quasi-ballistic photons travel the shortest possible path length in the sample and are therefore absorbed to a relatively small extent. Interfering substances having a strong light absorption which are contained in the sample (in the case of tissue samples mainly haemoglobin and water) therefore cause relatively small interference with the measurement. The same effect is also the basis why the measuring light, despite the strong absorption of these interfering substances, can penetrate relatively deep into the sample. Hence, for example in the skin, layers are reached in which the concentration of the glucose varies in a significant manner. Furthermore, due to the straight-line path of the photons detected with the method according to the invention, the length of the optical light path in the sample is defined. It corresponds to twice the measuring depth d.

Of particular importance for the advantages achieved with the invention is an effect which will now be explained with reference to FIGS. 2 to 4. Under the measuring conditions applying to the invention the attenuation of the irradiated light intensity is determined mainly by the scattering coefficient $\mu_s$ and to only a lesser extent by the absorption coefficient $\mu_a$. Furthermore it must be borne in mind, that in the case of the depth-selective quasi-ballistic measuring regime of the invention, in contrast to a diffuse measuring regime, the light transmission is not described by the corrected scattering coefficient $\mu_s'$, but by the uncorrected scattering coefficient $\mu_s$, which is always greater than $\mu_s'$. It was found in the context of the invention that the uncorrected scattering coefficient and hence the measuring signal depends under the measuring conditions according to the invention to a relatively high extent on the concentration of the analyte. Therefore with the invention the analyte-specific signal variation is relatively large.

FIGS. 2a and 2b show the graph of the phase refractive index $n_p$ of a glucose solution in water for a glucose concentration of 6.25 mmol (millimol per liter) and 100 mmol as a function of the wavelength L in $\mu$m. These measurement results were obtained with an interferometer, with which the dependence of the phase on the doppler frequency resulting from the movement of the interferometer mirror can be determined. The dependence of the phase refractive index on the wavelength shown in FIGS. 2a and 2b can be calculated directly therefrom. Of particular interest is the slope of the graph in the region of the absorption maximum at 2.15 $\mu$m (shown in dashes in FIG. 2b). This slope corresponds to the group refractive index $n_G$, which determines the scattering behaviour in the scattering matrix.

FIG. 3 shows in the form of bar charts for three different substances, namely the analyte glucose (GLUC) and the two important interfering substances NaCl and lactate (LAC), the group refractive index $n_G$ for each of four different light wavelengths. FIG. 4 shows the differential refractive index, referred to the wavelength. The group refractive index differences $dn_G$ are plotted for the three substances and for the wavelength pairs 1.6 $\mu$m minus 1.3 $\mu$m and 2.135 $\mu$m minus 1.75 $\mu$m.

The absolute values of the group refractive index $n_G$ shown in FIG. 3 are highest for glucose, but are also considerable for the interfering substances NaCl and lactate. The differential refractive index represented in FIG. 4 shows a far clearer differentiation. In particular, a value for $dn_G$ of $5 \times 10^{-6}$/mmol, for example, is obtained for the shown wavelength pair 2.135 $\mu$m minus 1.75 $\mu$m. In this region a solution of glucose in water has an absorption maximum. From published literature data it can be derived that the differential absorption coefficient (i.e. the change in the absorption as a function of a change in the glucose concentration) is about $d\mu_a = 2 \times 10^{-4}$/mmol (for a wavelength L=2.15 $\mu$m).

In a scattering matrix the light scattering, i.e. the scattering coefficient $\mu_s$, depends on the refractive index, the size and concentration of the scattering particles, and on the refractive index of the medium in which the scattering particles are distributed. If these quantities are known, $\mu_s$ can be determined by means of the Mie theory, for which type of calculations computer programs are available. In the case of skin tissue as scattering matrix, the following approximate values can be assumed:

refractive index of the scattering particles (cells): 1.41 particle size: 10 $\mu$m concentration: 5% refractive index of the interstitial fluid: 1.38.

According to the Mie calculation these numerical values lead to a scattering coefficient of 6.8 mm$^{-1}$, i.e. a value that is in agreement with measurement results for the (uncorrected) scattering coefficient $\mu_s$ in tissue. This confirms that the numerical values assumed make sense. From the above-mentioned value of the refractive index difference (differential refractive index) $dn_G = 5 \times 10^{-6}$/mmol one may obtain according to the Mie calculation a corresponding differential scattering coefficient $d\mu_s = 2.015 \times 10^{-3}$/mmol. This value is 10 times as high as the above-mentioned differential change in the absorption coefficient ($d\mu_a = 2 \times 10^{-4}$/mmol).

It has thus been shown that the measuring arrangement according to the invention detects a measurement quantity which depends more sensitively on changes in the analyte concentration than the optical absorption conventionally measured in a diffuse measuring regime according to the prior art.

The measuring conditions and the method of evaluation can be optimized in view of the knowledge derived from the invention, taking into account the following considerations.

Preferably at least two detection measurements with different light wavelengths are performed. It is further preferred to calculate in the evaluation step a quotient of the measured values at the two different wavelengths and to derive the information on the presence of the analyte on the basis of the quotient. Thereby an interfering background absorption can be largely eliminated if the total optical absorption of the sample changes to a far lesser extent than the scattering coefficient. This can be explained by the fact that the overall attenuation of the light intensity as a function of the measuring depth d is in the case of ballistic photons proportional to $e^{-(\mu_s+\mu_a)d}$. Therefore $\mu_a$ can be eliminated if a quotient is formed from the measured intensity values from two measurements with constant $\mu_a$ values.

The measuring depth d is in the case of skin tissue choosen based on medical considerations. In order to detect a tissue layer whose glucose concentration can provide valuable information in medical terms, the measuring depth should be at least about 0.3 mm. Greater measuring depths lead, as described, to an exponential decrease in the intensity of the measuring signal. At the present time a measuring depth of around 1.5 mm is regarded as the maximum upper limit in skin tissue.

Preferably at least two measurements are made, in which the measuring depth coinciding with the depth of focus d is different. It is particularly preferable to perform measurements with the same light wavelengths $L_1$ and $L_2$ at each of the different measuring depths $d_1$ and $d_2$. It is thus possible in an advantageous manner to prevent measuring errors which are attributable to fluctuations in the intensity of the irradiated primary light $I_0$, Fluctuations of this kind may be caused not only by fluctuations in the intensity of the light transmitters 10. In the case of measurements on the skin, a fundamental problem is caused, in fact, by the passage of the light out of the measuring head 2 through the interface 5 into the sample 6 ("coupling"). Even small changes in the position of the measuring head can cause changes of the intensity of the primary light irradiated into the sample 6 which are greater than the measuring signal. These measuring errors can be eliminated with the measuring arrangement according to the invention if measurements are made at two different measuring depths and a quotient is derived from the measured intensity signals (at the same wavelength in each case).

It is also particularly advantageous if one of the two measurements is made with a measuring depth as small as possible and the second measurement with a measuring depth as large as possible. The small measuring depth should lie below the epidermis layer. A range between 0.3 mm and 0.5 mm can be given as a guide value. The maximum size of the second (greater) measuring depth is determined mainly by the intensity of the measuring signal. The difference between the two measuring depths should be at least 0.3 mm.

The size of the light entry aperture in front of the detector is also of importance. In the literature the term "true confocal imaging" has been coined to describe ideal conditions for a confocal imaging arrangement. Further details can be found in the article by Sheppard et al. cited further above. Within the scope of the invention preferably a substantially larger light entry aperture is used. It should preferably be at most five times as large as that required for a true confocal imaging (in accordance with the formulae given in the article by Sheppard et al.). In general the diameter of the light entry aperture in front of the detector should be below 0.1 mm, preferably below 0.05 mm.

In practice it is most advantageous not only to work with a single confocal arrangement and a single range of focus, but to use a large number of confocal arrangements in the form of an "array", by means of which the primary light is focussed onto a large number of ranges of focus in the scattering matrix and these ranges of focus are each imaged onto a detector through a particular aperture diaphragm. In this way the total light intensity is increased with a maximum power density given for medical reasons. In addition, measuring errors due to microheterogeneities in the skin are largely eliminated by averaging.

The desired analytical information is, as mentioned, determined by means of an evaluation algorithm, which links on the basis of a calibration the measured values of the measured measurement quantity with concentration values. In the present case this linking can be a simple one-dimensional evaluation curve which assigns a concentration value to each of the quotients from the measured intensity values of two wavelengths or two measuring depths.

In recent times increasing use has been made of more complex mathematical techniques to improve the correlation in analytical procedures between the measurement quantities (input variables) and the concentration sought (output variable) and thereby to achieve a better analytical accuracy. These techniques include in particular multilinear and non-linear algorithms, which link several factors which are required for the evaluation of the analytical measurement. In the present case it may be advantageous, for example, to carry out in each measuring step a large number of measurements at different light wavelengths and to correlate these measured values as a whole with the respective concentration value by means of a suitable numerical algorithm. Suitable algorithms are known and in some cases available commercially as computer programs. If such a technique is used, it may be advantageous to use the measuring signals for at least two different wavelengths and at least two different measuring depths directly as input variables (i.e. without prior quotient formation).

Although the above explanations relate mainly to glucose as an analyte, the invention is also applicable to other analytes, in particular if the following preconditions apply: small specific optical absorption of the analyte against a large absorption background; overall absorption of the sample in the investigated wavelength range largely constant; strong wavelength-dependent variation of the optical absorption (and hence also of the refractive index of the interstitial fluid) in the investigated wavelength range. Alcohol may be mentioned as a possible analyte with such properties. The suitability of the invention for a particular analysis can be tested on an individual basis by an experimental testing of the arrangement according to the invention over a greater light wavelength range, and an optimum wavelength range established.

FIG. 5 shows an embodiment in which a low coherence reflecto-metric measurement is carried out as an additional depth selection means in the measuring step. Such a technique is also referred to in English as "LCI (low coherence interferometry) reflectometric measurement" or else as "optical coherence domain reflectometry (OCDR)". Interferometric measuring techniques of this kind are known for various purposes. Reference may be made for example to the publications:

"Measurement of optical properties of biological tissues by low-coherence reflectometry", by Schmitt et al., Applied Optics, 32 (1993), 6032–6042, as well as WO 92/19930 and the already mentioned WO 95/30368.

It is essential for an LCI measurement that a part of the light emitted by a light transmitter emitting over a broad spectral band is separated by a beam splitter, is fed on a reference light path to an optically reflecting element, is reflected from the latter and is combined in front of the detector with the measuring light path in such a way that the secondary light and the reference light interfere with each another. The light receiver measures an interference signal if the optical light path length in the reference arm (from the beam splitter up to the reflecting element) differs from the optical path length of the measuring light path from the beam splitter up to the reflection point in the sample by not more than the coherence length of the light source. An interference signal is only measured if this condition is fulfilled. This can be used to limit the investigation of a sample to a particular measuring depth d.

In the embodiment according to FIG. 5 an additional light path is provided which is formed by light reflected to the left in the BSC 15 and forms the reference arm 30 of an interferometer arrangement. The reference light is reflected by a movable mirror 31 and falls back in the opposite direction into the BSC 15, reaching the detector-side light entry aperture (diaphragm pinhole 22) via the secondary light path 19. The interference condition is fulfilled if the optical light paths in the reference arm 30 (up to the surface of the mirror 31) and in the sample arm 32 (up to the measuring depth d) are the same. The selective detection of the light reflected from the measuring depth d can therefore be improved by the adjustment of the mirror 31. Further details on the use of the techniques for performing the LCI method can be found in the literature references cited above.

A further special feature of the embodiment shown in FIG. 5 is that both the light irradiation means 8 and the detection means 9 comprise optical fibres 33 and 34 respectively, through which the light is passed from light transmitters (not shown) to the BSC and from there to detectors (likewise not shown) It is not of fundamental importance for the invention whether the primary light (as in FIG. 1) is irradiated into the measuring arrangement directly from the light transmitters 10 and is detected directly by detectors 20 or whether light guides (as in FIG. 5) are used. It is critical only that the effective light exit aperture 12, from which the primary light enters the optical system, and the effective light entry aperture 24 in the secondary light path 19 have sufficiently small dimensions to permit a sufficiently sharp focussing both in the primary light path and in the secondary light path. The limitation of the primary-side light exit aperture and the secondary-side light entry aperture can be realised in different ways, for example by diaphragm pinholes as shown or else by the correspondingly dimensioned exit end of a light-conducting fibre or by the size of the light-sensitive surface of a detector.

In the arrangement with a BSC shown in FIGS. 1 and 4, there is a problem with Fresnel reflections caused by the sudden change of the refractive index at the boundaries of the BSC. Light is thereby for example reflected from the boundary surface 29 of the BSC through which the measuring light exits into the sample (FIG. 5). This strong reflection signal can cause overload of the detector. To prevent this, the embodiment of FIG. 6 shows an arrangement in which the axis AP of the primary light beam 14 is inclined relative to the corresponding limiting surface 29 at an angle Θ which is less than 90°. The light beam 35 reflected specularly as a result of Fresnel reflection consequently does not impinge on the detector 20.

In FIG. 6 the deviation of the angle Θ is shown highly exaggerated. In practice a very small deviation of less than 1° suffices to ensure that specularly reflected light no longer impinges on the light-detector-side light entry aperture 24.

With the embodiments of FIGS. 1, 5 and 6 the secondary light reflected back coaxially out of the region of focus is detected (i.e. the axis AP of the primary light and the optical axis AS of the secondary light coincide between the optically focussing element and the focal point). By contrast, FIG. 7 shows an embodiment in which the optically focussing elements of the irradiation means 8 and of the detection means 9 are separate, whereby the optical axis on which the light is irradiated into the sample and the optical axis on which the light is detected differ. In the embodiment shown the primary light irradiated by a light-conducting fibre 32 for each region of focus 17 of an array passes through a first lens 40 and a second lens 41, which has twice as large a diameter as the first lens. The focussed light penetrates the matrix 6 asymmetrically. After backscatter the secondary light passes through the second lens 41 and a third lens 42 in reverse sequence. In this embodiment the system of lenses 40, 41, 42 again makes sure that the primary light 14 is focussed onto the region of focus 17 and this region of focus 17 is imaged onto the detector-side light entry aperture 24. The use of a total of three lenses with the arrangement shown has the advantage that commercially available microlens arrays can be used. Conversely, if the lenses are arranged obliquely (i.e. not parallel with the surface 5 of the matrix 6, which is also possible in principle), customized manufacture of the microlens arrangement is required.

With the embodiment according to FIG. 7 no interference problems involving Fresnel back reflection can occur, since no light reflected specularly from a straight face reaches the detector. Optical errors in the lenses (in particular aberration errors) lead to distortions and hence to a less sharp definition of the region of focus 17. This, however, is not normally a problem. Known optical correction measures can be applied if necessary.

FIGS. 8 and 9 show two possible ways to allow measurement with a plurality of light wavelengths with the general layout of FIG. 7.

In FIG. 8 three laser diodes are used as primary light transmitters 10a, 10b, 10c, which emit light at different wavelengths and are preferably integrated on a common substrate as an integrated optical system. These three light transmitters radiate through different angles of incidence onto a half-lens 45a, which collimates the light at different angles. An optical grating 46 is arranged below the half-lens 45a, whose grating constant is so choosen, that the collimated rays of different light wavelength impinging at different angles are transformed into a common (collimated) ray along the optical axis. This ray is focussed onto a light exit aperture 12 through a second half-lens 45b.

On the detector side there is a corresponding arrangement consisting of two half-lenses 47a and 47b, the grating 46 and detectors 20a, 20b, 20c for the various light wavelengths. The two half-lenses 45a, 45b, 47a, 47b form with the grating a sandwich which can be made in a simple manner by the use of microlens structures.

In the embodiment according to FIG. 9 the three laser diodes are replaced by a single laser diode 10 emitting broad band light radiation. Here the wavelength selectivity is effected by the grating and the three detectors 20a, 20b, 20c arranged at different angles behind the grating. This arrangement is simpler than that of FIG. 8 but the wavelength selectivity is reduced.

FIG. 10 shows the manner in which a low coherence reflecto-metric measurement is possible as an additional depth selection means with an embodiment according to FIGS. 7 to 9. Only the central rays of the light beams are shown. A horizontally positioned semireflective mirror 48 serves here as a beam splitter for generating a reference beam. The reflected light beam 50a impinges onto a reference reflector 51, whose distance from the semireflective mirror 48 corresponds to the distance of the region of focus 17 from the semireflective mirror 48. On grounds of symmetry the light impinging onto the reference mirror 51 is focussed in the same manner as the light irradiated into the sample 6. The light reflected from the reference reflector 51 falls back as a light beam 50*b* onto the semireflective mirror 48 and is reflected from there in the direction of the reflector. In this arrangement the beams 50*a* and 50*b* form the reference arm 50 of the interferometer arrangement. The reference light can be modulated by a vibrating reference reflector 51. Alternatively an LCD element can be arranged in the light beam and controlled with a suitable modulation frequency in such a way that the reference light is modulated.

We claim:

1. Method for determining an analyte in a scattering, in particular biological, matrix, in which in a detection step detection measurements are carried out in which light is irradiated through an interface limiting the scattering matrix as primary light into the matrix and light leaving the scattering matrix through the interface is detected by a detector as secondary light, in order to determine as a measurement quantity a measurable physical property of the light which is variable due to the interaction of the light with the matrix, said interaction including optical absorption and in an evaluation step information on the presence of the analyte in the matrix is determined on the basis of a measured value of the measurement quantity measured in the detection step, wherein, using a confocal measuring arrangement, a first depth selection means is provided such that the primary light is focussed by means of a primary light optically focussing element onto a region of focus lying in the matrix at a depth of focus below the interface, the region of focus is imaged by means of a secondary light optically focussing element onto a light entry aperture arranged in the light path of the secondary light to the detector, the detection of the secondary light thereby being concentrated on the region of focus, wherein for generating a measurement signal allowing a selective analysis of an analyte which causes only a small share of the optical absorption, light reflected from a defined measuring depth below the interface is detected selectively as secondary light by a second depth selection means, the defined measuring depth coinciding with the depth of focus, and wherein the analyte comprises glucose.

2. Method according to claim 1, wherein the measuring depth coinciding with the depth of focus is at least 0.3 mm and at most 1.5 mm.

3. Method according to claim 1, wherein the wavelength of the light in at least one of the detection measurements is between 2.0 μm and 2.4 μm.

4. Method according to claim 1, wherein at least two detection measurements are made with different light wavelengths.

5. Method according to claim 4, wherein in the evaluation step a quotient of the measured values at the two different wavelengths is obtained and the information on the presence of the analyte is determined on the basis of the quotient.

6. Method for determining an analyte in a scattering, in particular biological, matrix, in which in a detection step detection measurements are carried out in which light is irradiated through an interface limiting the scattering matrix as primary light into the matrix and light leaving the scattering matrix through the interface is detected by a detector as secondary light, in order to determine as a measurement quantity a measurable physical property of the light which is variable due to the interaction of the light with the matrix, and in an evaluation step information on the presence of the analyte in the matrix is determined on the basis of a measured value of the measurement quantity measured in the detection step, the primary light being focussed by means of a primary light optically focussing element onto a region of focus lying in the matrix at a depth of focus below the interface, and the region of focus being imaged by means of a secondary light optically focussing element onto a light entry aperture arranged in the light path of the secondary light to the detector, the detection of the secondary light thereby being concentrated on the region of focus, wherein light reflected from a defined measuring depth below the interface is detected selectively as secondary light by means of a depth selection means, the defined measuring depth coinciding with the depth of focus, and wherein the primary light is focussed by means of an array of primary light optically focussing elements onto a plurality of regions of focus located at the same depth of focus below the interface and the plurality of the regions of focus is imaged by means of a corresponding number of secondary light optically focussing elements onto respective light entry apertures arranged in the light path to the detector.

7. Method according to claim 6, wherein the primary light is focussed onto at least ten different regions of focus.

8. A method as recited in claim 6, wherein at least two detection measurements are made with different light wavelengths.

9. A method as recited in claim 8, wherein in the evaluation step, a quotient of the measured values at the two different wavelengths is obtained, and the information on the presence of the analyte is determined on the basis of the quotient.

10. Method for determining an analyte in a scattering, in particular biological, matrix, in which in a detection step detection measurements are carried out in which light is irradiated through an interface limiting the scattering matrix as primary light into the matrix and light leaving the scattering matrix through the interface is detected by a detector as secondary light, in order to determine as a measurement quantity a measurable physical property of the light which is variable due to the interaction of the light with the matrix, and in an evaluation step information on the presence of the analyte in the matrix is determined on the basis of a measured value of the measurement quantity measured in the detection step, the primary light being focussed by means of a primary light optically focussing element onto a region of focus lying in the matrix at a depth of focus below the interface, and the region of focus being imaged by means of a secondary light optically focussing element onto a light entry aperture arranged in the light path of the secondary light to the detector, the detection of the secondary light thereby being concentrated on the region of focus, wherein light reflected from a defined measuring depth below the interface is detected selectively as secondary light by means of a depth selection means, the defined measuring depth coinciding with the depth of focus, and wherein at least two detection measurements are made, in which the measuring depth coinciding with the depth of focus is different.

11. Method according to claim 10, wherein the measuring depth coinciding with the depth of focus differs by at least 0.3 mm in the at least two detection measurements.

12. A method as recited in claim 10, wherein at least two detection measurements are made with different light wavelengths.

13. A method as recited in claim 12, wherein in the evaluation step, a quotient of the measured values at the two different wavelengths is obtained, and the information on the presence of the analyte is determined on the basis of the quotient.

14. Method for determining an analyte in a scattering, in particular biological, matrix, in which
- in a detection step detection measurements are carried out in which light is irradiated through an interface limiting the scattering matrix as primary light into the matrix and light leaving the scattering matrix through the interface is detected by a detector as secondary light, in order to determine as a measurement quantity a measurable physical property of the light which is variable due to the interaction of the light with the matrix, and
- in an evaluation step information on the presence of the analyte in the matrix is determined on the basis of a measured value of the measurement quantity measured in the detection step,
- the primary light being focussed by means of a primary light optically focussing element onto a region of focus lying in the matrix at a depth of focus below the interface, and
- the region of focus being imaged by means of a secondary light optically focussing element onto a light entry aperture arranged in the light path of the secondary light to the detector, the detection of the secondary light thereby being concentrated on the region of focus,
- wherein light reflected from a defined measuring depth below the interface is detected selectively as secondary light by means of a depth selection means, the defined measuring depth coinciding with the depth of focus, and wherein the measuring step comprises providing means for performing a low coherence reflectometric measurement as the depth selection means.

15. A method as recited in claim 14, wherein at least two detection measurements are made with different light wavelengths.

16. A method as recited in claim 15, wherein in the evaluation step, a quotient of the measured values at the two different wavelengths is obtained, and the information on the presence of the analyte is determined on the basis of the quotient.

17. Method for determining an analyte in a scattering, in particular biological, matrix, in which
- in a detection step detection measurements are carried out in which light is irradiated through an interface limiting the scattering matrix as primary light into the matrix and light leaving the scattering matrix through the interface is detected by a detector as secondary light, in order to determine as a measurement quantity a measurable physical property of the light which is variable due to the interaction of the light with the matrix, and
- in an evaluation step information on the presence of the analyte in the matrix is determined on the basis of a measured value of the measurement quantity measured in the detection step,
- the primary light being focussed by means of a primary light optically focussing element onto a region of focus lying in the matrix at a depth of focus below the interface, and
- the region of focus being imaged by means of a secondary light optically focussing element onto a light entry aperture arranged in the light path of the secondary light to the detector, the detection of the secondary light thereby being concentrated on the region of focus,
- wherein light reflected from a defined measuring depth below the interface is detected selectively as secondary light by means of a depth selection means, the defined measuring depth coinciding with the depth of focus, and wherein the measuring step comprises providing means for irradiating the primary light in a form of a short light pulse and the secondary light is measured within a defined time window, as the depth selection means.

18. A method as recited in claim 17, wherein at least two detection measurements are made with different light wavelengths.

19. A method as recited in claim 18, wherein in the evaluation step, a quotient of the measured values at the two different wavelengths is obtained, and the information on the presence of the analyte is determined on the basis of the quotient.

20. Apparatus for determining an analyte in a scattering matrix, said apparatus comprising:
- a measuring head with a sample contact surface adapted to be placed against an interface of the scattering matrix,
- light irradiating means with a light transmitter for irradiating primary light into the scattering matrix through the sample contact surface and the interface,
- detection means with a detector for detecting secondary light leaving the scattering matrix through the interface and the sample contact surface and
- evaluation means for deriving the information on the presence of the analyte in the matrix from the measuring signal of the detector,
- in which the irradiation means and the detection means each comprise, an optically focussing element, a primary light optically focussing element of the irradiation means focusses the primary light onto a region of focus lying in the matrix at a depth of focus below the interface, and a secondary light optically focussing element of the detection means images the region of focus onto a light entry aperture arranged in the light path of the secondary light to the detector, whereby the detection of the secondary light is concentrated on the region of focus,
- wherein an additional depth selection means is provided for selectively detecting light as secondary light reflected from a defined measuring depth, the measuring depth coinciding with the depth of focus, wherein said apparatus performs
  - a detection step wherein detection measurements are carried out in which light is irradiated through the interface as the primary light into the matrix, and the secondary light is detected by the detector leaving the matrix, to determine a measurable physical property of the light which is variable due to interaction of the light with the matrix as a measurement quantity, and an evaluation step wherein information on presence of the analyte in the matrix is determined based upon a measured value of the measurement quantity measured in the detection step, with the primary light being focused by the primary light optically focussing element onto the region of focus lying in the matrix at the depth of focus below the interface, with the region of focus being imaged by the secondary light optical focussing element onto the light entry aperture arranged in the light path of the secondary light to the detector, with the detection of the secondary light being concentrated on the region of focus, and wherein the light reflected from the defined measuring depths below the interface is detected selectively as secondary light by the additional depth selection means, with the defined depth coinciding with the depth of focus.

21. Apparatus according to claim 20, wherein the diameter of the light entry aperture is less than 0.1 mm.

22. Apparatus according to claim 20, wherein both the irradiation means and the detection means comprise an array of optically focussing elements by means of which the primary light is focussed onto a plurality of regions of focus and the plurality of the regions of focus is imaged onto respective light entry apertures in front of a detector.

23. Apparatus according to claim 22, wherein the array of optically focussing elements is a microlens array.

24. Apparatus according to claim 22, wherein a plurality of detectors is integrated monolithically on a semiconductor chip.

25. Apparatus according to any one of claim 22, wherein a plurality of light transmitters is integrated monolithically on a semiconductor chip.

26. Apparatus according to claim 20, wherein the primary light optically focussing element and the secondary light optical focussing element comprise the same optically focussing element forming part both of the irradiation means and of the detection means, so that the optical axis of the primary light and the optical axis of the secondary light coincide between the optically focussing element and the region of focus, and on the side of the focussing element facing away from the matrix a beam splitter is disposed by means of which the secondary light is branched to the detector.

27. Apparatus according to claim 20, wherein the irradiation means and the detection means comprise separate optically focussing elements, wherein the optical axis, on which the primary light is irradiated into the matrix, and the optical axis, on which the secondary light is detected, are different.

28. Apparatus according to claim 20, wherein it includes as the depth selection means a low coherence reflectometric measuring device.

29. Apparatus according to claim 20, wherein it includes as the depth selection means a device for irradiating the primary light in the form of a short light pulse and for measuring the secondary light within a defined time window.

* * * * *